(12) United States Patent
Burton

(10) Patent No.: US 7,204,250 B1
(45) Date of Patent: Apr. 17, 2007

(54) BIO-MASK

(75) Inventor: David Burton, Camberwell (AU)

(73) Assignee: Compumedics Limited, Abbotsford (AU)

( * ) Notice: Subject to any disclaimer, the term of this patent is extended or adjusted under 35 U.S.C. 154(b) by 0 days.

(21) Appl. No.: 09/465,054

(22) Filed: Dec. 16, 1999

(51) Int. Cl.
*A62B 9/00* (2006.01)
*A62B 18/02* (2006.01)

(52) U.S. Cl. .............................. 128/205.23; 128/206.21

(58) Field of Classification Search ........... 128/704.21, 128/206, 21, 207.11, 205.23, 206.12, 206.18, 128/206.21, 206.27, 206.28; 600/508, 529, 600/537, 538, 544, 545, 534
See application file for complete search history.

(56) References Cited

U.S. PATENT DOCUMENTS

| | | | | |
|---|---|---|---|---|
| 3,606,881 A | * | 9/1971 | Woodson | 600/392 |
| 4,875,477 A | | 10/1989 | Waschke et al. | 128/206.21 |
| H1039 H | * | 4/1992 | Tripp et al. | 128/206.28 |
| 5,131,399 A | | 7/1992 | Sciarra | 128/671 |
| 5,134,995 A | * | 8/1992 | Gruenke et al. | 128/204.23 |
| 5,243,971 A | | 9/1993 | Sullivan et al. | 128/205.25 |
| 5,293,867 A | | 3/1994 | Oommen | |
| 5,353,788 A | * | 10/1994 | Miles | 128/204.23 |
| 5,353,793 A | * | 10/1994 | Bornn | 600/386 |
| 5,503,146 A | | 4/1996 | Froehlich et al. | 128/204.23 |
| 5,503,147 A | * | 4/1996 | Bertheau | 128/207.11 |
| 5,507,716 A | | 4/1996 | LaBerge et al. | 600/27 |
| 5,617,849 A | * | 4/1997 | Springett et al. | 128/206.24 |
| 5,673,692 A | * | 10/1997 | Schulze et al. | 600/301 |
| 5,860,417 A | | 1/1999 | Kettl et al. | 128/201.19 |
| 6,000,395 A | * | 12/1999 | Brown | 128/202.19 |
| 6,029,665 A | * | 2/2000 | Berthon-Jones | 128/204.23 |
| 6,032,065 A | * | 2/2000 | Brown | 600/383 |
| 6,097,981 A | * | 8/2000 | Freer | 600/545 |
| 6,199,550 B1 | * | 3/2001 | Wiesmann et al. | 128/204.23 |
| 6,240,921 B1 | * | 6/2001 | Brydon et al. | 128/205.23 |
| 6,357,440 B1 | * | 3/2002 | Hansen et al. | 128/206.19 |

FOREIGN PATENT DOCUMENTS

GB 2294642 5/1996
WO WO 97/33641 9/1997

* cited by examiner

*Primary Examiner*—Teena Mitchell
(74) *Attorney, Agent, or Firm*—Fulbright & Jaworski L.L.P.

(57) ABSTRACT

The invention relates to a breathing mask for use in monitoring a patient. The mask can have sensors on the body of the mask and on the associated straps or caps. The mask can be used to monitor breathing problems or to monitor a patient during anesthesia. The data acquired from the mask sensors and related sensors can be stored or fed into a computer to analyze the patient's condition and provide feedback information.

24 Claims, 4 Drawing Sheets

BIO-MASK

BACKGROUND OF THE INVENTION

1. Field of the Invention

This invention relates to a breathing mask with built in sensors for monitoring patients with sleep apnea, breathing disorders for use during anesthesia or ventilation support.

2. Description of the Related Art

Masks such as shown in U.S. Pat. No. 5,243,971 for applying a positive pressure to patients with apnea and other breathing disorders have been developed. These masks provide seals for preventing air from escaping from the mask at the junction of the mask and face. Other types of masks for gas delivery to a patient are also in common use.

Measuring air flows to a patient has been accomplished by metering sensors in the air supply connected to the mask as in U.S. Pat. No. 5,503,146 or by belts around the patients chest to measure his breathing as in U.S. Pat. No. 5,131,399.

Some devices such as in U.S. Pat. No. 5,507,716 provide sensors combined with sleep masks for covering the eyes of a patient. However there is no known example of sensors built into breathing masks for monitoring or studying patients with breathing disorders.

Currently if a patient is to be carefully monitored a plurality of electrodes or sensors would have to be individually applied to the patient and wired to recording equipment. The plurality of sensors and tangle of ensuing wires impede the usage of such monitoring equipment. Sensors providing useful information include Electro-encephalogram (EEG), electromyography (EMG), electro-oculogram (EOG), electro-cardiogram (ECG), Pulse Transit Time (PTT), gas flow sensors, temperature sensors, microphones, blood oxygen meters, blood pressure sensors, pulse sensors, patient movement, position, light, activity sensors, mask leakage, mask pressure, eye movement (PVD or Piezo) and other means of gathering data about the patient or his environment.

It is very inconvenient for the patient and the health care worker to attach a series of different devices to a patient to monitor a plurality of different parameters simultaneously. Therefore a single device for easily measuring a plurality of parameters is desired.

SUMMARY OF THE INVENTION

The invention relates to providing sensors in breathing masks to make it easy to monitor a patient. The mask has a soft pliable seal material around its perimeter in contact with the patient's face to form a secure seal therewith. Sensors may be recessed into the soft pliable seal material at the surface for contact with the skin of the user when the mask is applied to the user's face. The wiring for the sensors may be inside the soft pliable seal material insulating the wires from damage during use of the mask. Many sensors can be incorporated into the mask. Sensors may be placed on the perimeter or on other portions of the mask not in contact with the skin. Sensors may also be placed on straps or caps used in conjunction with the masks or on other devices used with the mask.

Monitoring of patients with sleep disorders, breathing disorders or for anesthesia is made easier and more convenient for the patient and for the health care provider since all the sensors needed are built into a mask which is easily and quickly placed on the patient with all the wiring to the sensors integral with the mask and accessed by a single plug.

The types of sensors on or in the mask and straps or caps connected to the mask include but are not limited to oximetery sensors, patient position sensors, eye movement sensors, leak detection sensors, EEG, EMG, EOG, ECG, PTT, microphones, pulse, blood pressure, oxygen saturation, temperature, movement sensors, position sensors, light sensors, leak detection sensors and gas delivery sensors.

Connections to outside sources of gases delivered to the mask are by a gas nozzle hook up on the mask. A connection to electrical power and data output cables are by a plug in to a cable connecting to the mask. Alternatively batteries in the mask and telemetry equipment in the mask can provide power and transmission of the data to a microprocessor or computer. For portability the microprocessor can be attached to the mask or be carried by the patient. Similarly a bottle of gas may be connected to the mask and carried by the patient to allow mobility of the patient while wearing the mask.

Unique applications for the bio-mask include the capability to apply anesthesia-depth monitoring while administering anesthesia gas to a subject. The ability to monitor the patient non-invasively with the bio-mask while at the same time administering the anesthesia gas to the patient provides a bio-feedback function for immediate and responsive anesthesia depth of the subject. The bio-mask can be used to determine the subject's sleep state by applying standard sleep staging criteria, such as that of R&K rules and/or the application of diagnostic techniques which analyze a number of EEG signals, such as Bispectral Analysis. The invention is unique in its capability to apply such analysis with the minimal-invasive application of a subject breathing mask.

R&K rules refer to "A Manual of Standardized Terminology, Technicques and Scoring System for Sleep Stages of Human Subject" by Rechtschaffen and Anothony Kales, Editors 1968 which is hereby made a part hereof and incorporated herein by reference.

OBJECTS OF THE INVENTION

It is an object of the invention to monitor a patient.

It is an object of the invention to provide data needed to help treat a patient.

It is an object of the invention to provide sensors for monitoring a patient in or on a breathing mask or on its associated parts.

It is an object of the invention to regulate the flow of gasses to a patient based on the data obtained from monitoring the patient.

It is an object of the invention to diagnose the patient based on data obtained from monitoring the patient.

It is an object of the invention to easily and quickly apply all the sensors needed for monitoring the patient.

Other objects, advantages and novel features of the present invention will become apparent from the following detailed description of the invention when considered in conjunction with the accompanying drawing.

DESCRIPTION OF THE PREFERRED EMBODIMENTS

Figure 1:
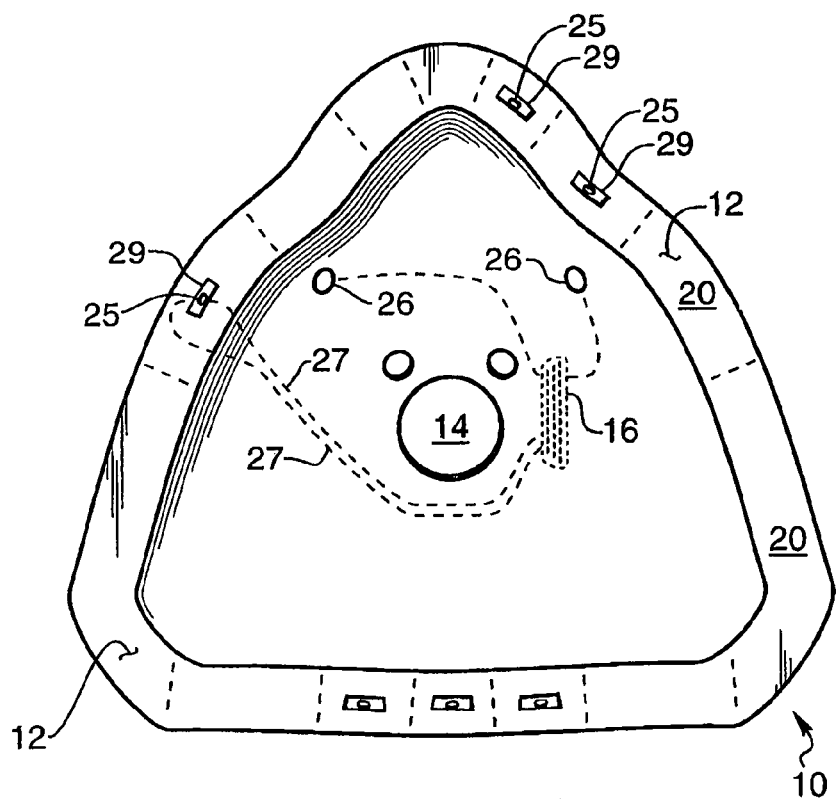
FIG. 1 shows a schematic view of the zones for sensors on the inside surface of a soft pliable material on the perimeter of the breathing mask.

FIG. 1 shows the inside of mask 10 including the perimeter surface 12 which contacts the patient's face. The perimeter surface 12 has a plurality of zones 20. Each zone 20 having a sensor 25 in a recess 29 for measuring a parameter of the patient to be monitored or other data such as gas leakage. Other sensors 26 are on the mask 10 but not in contact with the patient's skin. These sensors 26 measure patient data or related data such as ambient light, gas pressure in the mask or ambient temperature. The mask 10 has a gas connector 14 for connecting a hose 32 to provide a gas to the mask 10 and a mask interface connector 16 for plugging in a cable 30 for a power supply and for data transmission.

In some embodiments of the invention the sensors 25 do not require an outside source of power as the sensors such as heat sensors and light sensors generate current.

The mask perimeter surface 12 is preferably made out of a soft pliable material such as silicone rubber for making a good sealing contact with the face of the patient to prevent gas leakage. The material should be soft and pliable enough to follow the contours of the face. The perimeter surface preferably has recesses 29 on the surface for the insertion of sensors 25 so that the sensors can make contact with the patient's skin when the mask is pressed against the patient's face.

Figure 2:
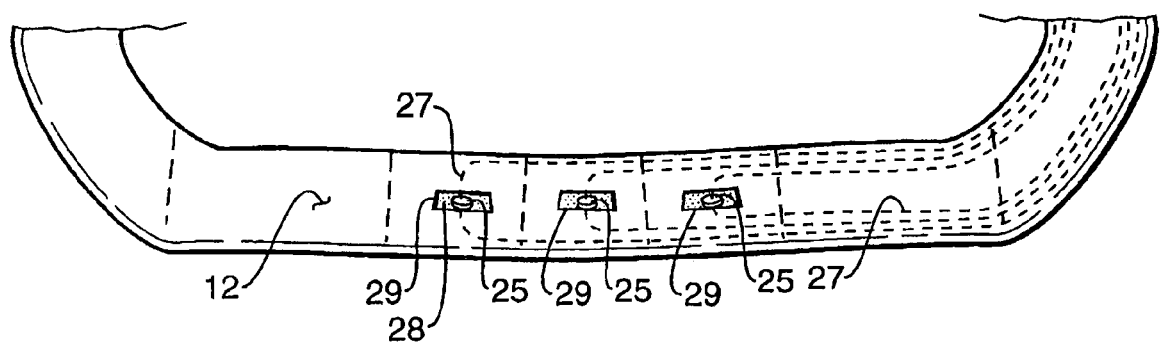
FIG. 2 shows a view of the sensors and wiring inside the soft pliable material on the perimeter of the breathing mask.
Figure 3:
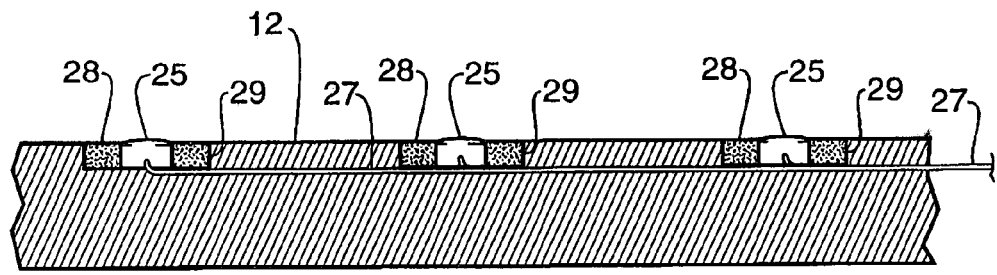
FIG. 3 shows a side schematic view of the sensors and the wiring inside of the soft pliable material on the perimeter of the breathing mask.

As seen in FIG. 3 a sensor or electrode 25 attachment to the mask 10 preferably utilizes a rubber compound 28 such as silicon or other food grade type rubber embedded with carbon or other conductive materials for electrical contact of skin to the mask. As shown in FIG. 2 the recesses 29 are large enough to have room to make electrical connections to leads 27, which are buried in the soft pliable material under the perimeter surface 12. The leads 27 are thus protected from damage and electrically insulated. Preferably the sensors 25 will plug into the leads 27 or printed circuits in the recesses 29. The leads 27 are preferably on printed circuits embedded in the mask or fine wires embedded in the mask and connect the sensors 25 to the mask interface connector 16.

Figure 5:
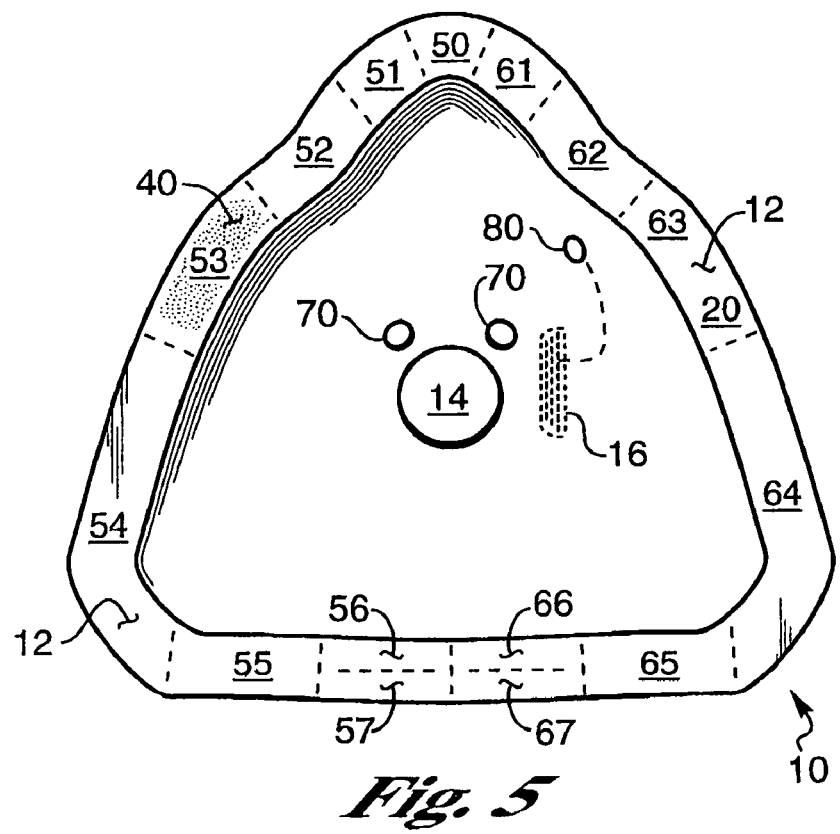
FIG. 5 shows a schematic view of the sensor zones on the perimeter of the breathing mask.

FIG. 5 shows conductive material 40 on the surface in zones 20, such as carbon embedded silicon, can be used on the surface of the perimeter 12 of mask 10 in separate zones 20 to conduct the electrical surface energy from the patient's face. The conductive material 40 is preferably moisture activated to improve the its electrical conductivity when in contact with the skin. The conductive material 40 may be applied for all electrode 25 contacts in all zones 20. Alternatively electrodes 25 may directly contact the patients face. The electrodes may also be inside of the soft pliable material on the perimeter 12 of the mask 10.

Figure 4:
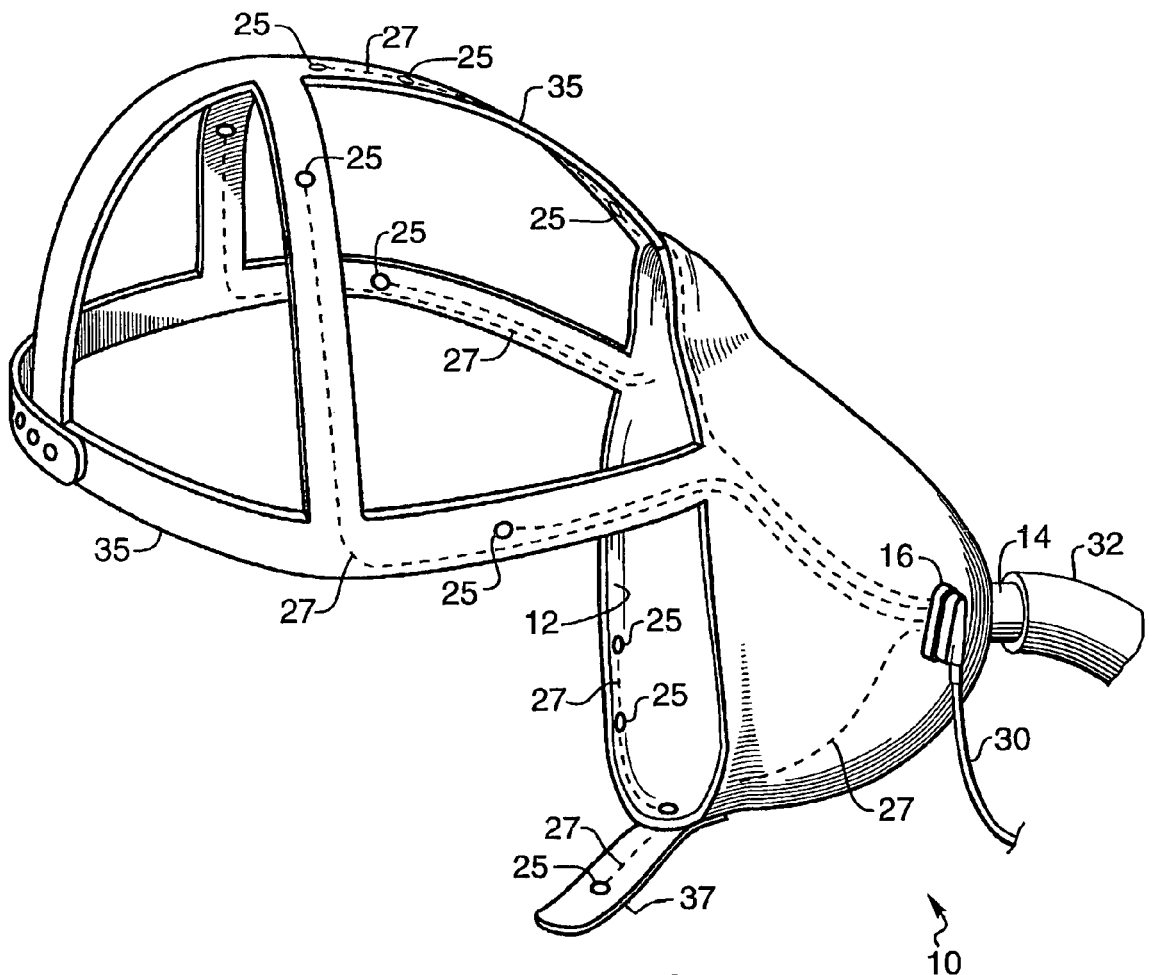
FIG. 4 shows a side schematic view of the straps connected to the mask with sensors embedded in the straps and the mask.

FIG. 4 shows a side view of the mask 10 and straps 35 used to keep the mask in place on a patient. The straps 35 have sensors 25 connected to leads 27, which connect the sensors to the mask interface connector 16 and to cable 30 for transmitting data to a computer or other device. The sensors 25 in the straps 35 may be electro-encephalogram EEG sensors for measuring brain waves. The straps 35 may be replaced with a cap having sensors therein. Alternatively a chin strap 37 may be used having sensors 25.

FIG. 5 shows an example of the types of sensors 25 used in zones 20 around the perimeter of the mask 10. Physiological signals from a patient's skin potential are detected by sensors in the zones 20 around perimeter 12 of mask 10. Conductive electrode paste may be used to improve the electrical contact between the sensors 25 and the surface of the skin. The conductive paste can assist in reducing the impedance between the face and the electrical output from the sensors 25 in zones 20. The conductive paste may also assist in preventing gas leaks.

As an example of a mask sensor layout the following sensors and their functions are described. However many other types of sensors and arrangements of the sensors are possible.

Zone 50 is an electro-oculogram (EOG) to obtain electrical eye movement reference signals from over the bridge of the nose.

Zone 51 is an EOG to detect electrical eye movement signals for the inner left eye and zone 61 is designated for electrical eye movement signals for the inner right eye. Eye movement data is related to stages of sleep such as rapid eye movement REM, which indicates a deep sleep state and dreaming.

Zone 52 is designated for an EOG to detect electrical eye movement signals for the outer left eye and zone 62 is designated for electrical eye movement signals for the outer right eye.

Zone 53 is designated for electro-myography (EMG) to detect electrical signals from muscle contractions in the upper left chin. Zone 63 is correspondingly for the upper right chin. Zones 54 and 64 are for the lower left and lower right chin respectively. The amplitude of the chin signals is proportional to the relaxation state and subsequent sleep state of the patient.

Zone 55 is the EMG for the upper left lip, giving information about sleep stages. It is proportional to the relaxation and sleep states of the patient. Zone 65 is the EMG for the upper right lip.

Zone 56 is the EMG for the left nasal inner mask it also provides signals for the lip movements and is proportional to the relaxation and sleep states of the patient. Similarly zone 66 is for the right nasal inner mask EMG.

Zones 57 and 67 are for the oral left and oral right outer mask EMG signals which are also proportional to the relaxation and sleep states of the patient.

Zone 70 is for pressure sensor ports for airflow determination.

Microphone 80 on the mask detects the patients breathing or snoring sounds.

Figure 6:
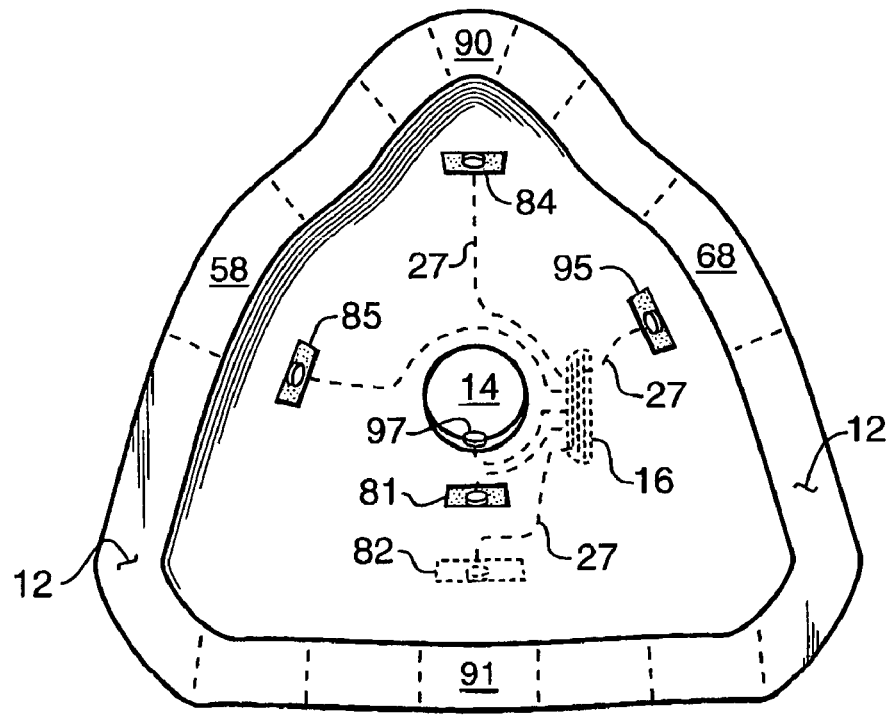
FIG. 6 shows a schematic view of the sensors on the inside surface of a breathing mask.

FIG. 6 shows an alternate embodiment where two sensors 58 and 68 are used to find the patient's electrocardiogram ECG. This data is also useful for monitoring a patient. The patient's heart functions provide a lot of useful data about the patient's condition. Pulse Transit Time (PTT) is the time it takes ECG pulses to travel from the heart to a sensor such as a sensor placed on the head, on a finger tip, or on the ear. PTT sensors can be in the mask, on sensors connected to the mask, or sensors used in conjunction with the mask. PTT measurements are used to determine patient arousals and qualitative blood pressure variation.

Thermal sensor 81 is used on the inside surface of the mask to detect nasal breathing. Thermal sensor 82 is used on the outside surface of the mask to detect oral breathing. The thermal sensitivity of the sensors 81 and 82 on the surface of the mask 10 opposite the nose or mouth indicates if the patient is breathing through his nose or mouth. The thermal sensors 81, 82 may alternatively be placed on the inside of the mask 10, on the outside of the mask 10, or inside of the material of mask 10 for detecting breathing. The thermal sensors 81, 82 may be a thermistor material, a thermocouple material or any other temperature sensitive material. The thermal sensors 81, 82 may be coatings on the inside of the mask, the outside of the mask or in the mask. The thermal sensors 81, 82 detect heat, which is proportional to the amount of breathing.

It is important to detect oral breathing for undetected or partially undetected oral breathing effects the integrity of the patient breathing gas breath monitoring and subsequently compromises the idea gas delivery to the patient. It is important to detect mouth breathing to assist in diagnosis of sleep disordered breathing. Further, control of a mask nasal ventilation is effected by mouth breathing.

A pressure sensor 84 measures the pressure inside of the mask to indicate if there is positive pressure inside of the mask and how much. A pressure drop may indicate a leak.

A surface reflective oximetry sensor 85 on the inside of the mask detects the patients pulse rate and oxygen saturation.

A surface blood pressure sensor 90 on the perimeter 12 of the mask 10 in contact with the patient can be used to monitor the patient's blood pressure.

A thermistor 91 on the perimeter 12 of the mask 10 in contact with the patient can be used to monitor the patients temperature.

A patient recycled air detection system having a sensor 95 on the inside surface of the mask detects the amount expired air from the patient remaining in the mask 10. High levels of expired gas in the mask indicates the mask is not being flushed out and may lead to problems if not enough fresh gas is introduced.

A patient back gas occurrence detector 97 in the mask hose connector 14 detects the amount of expired gas in the mask returning with newly delivered gas.

Figure 7:
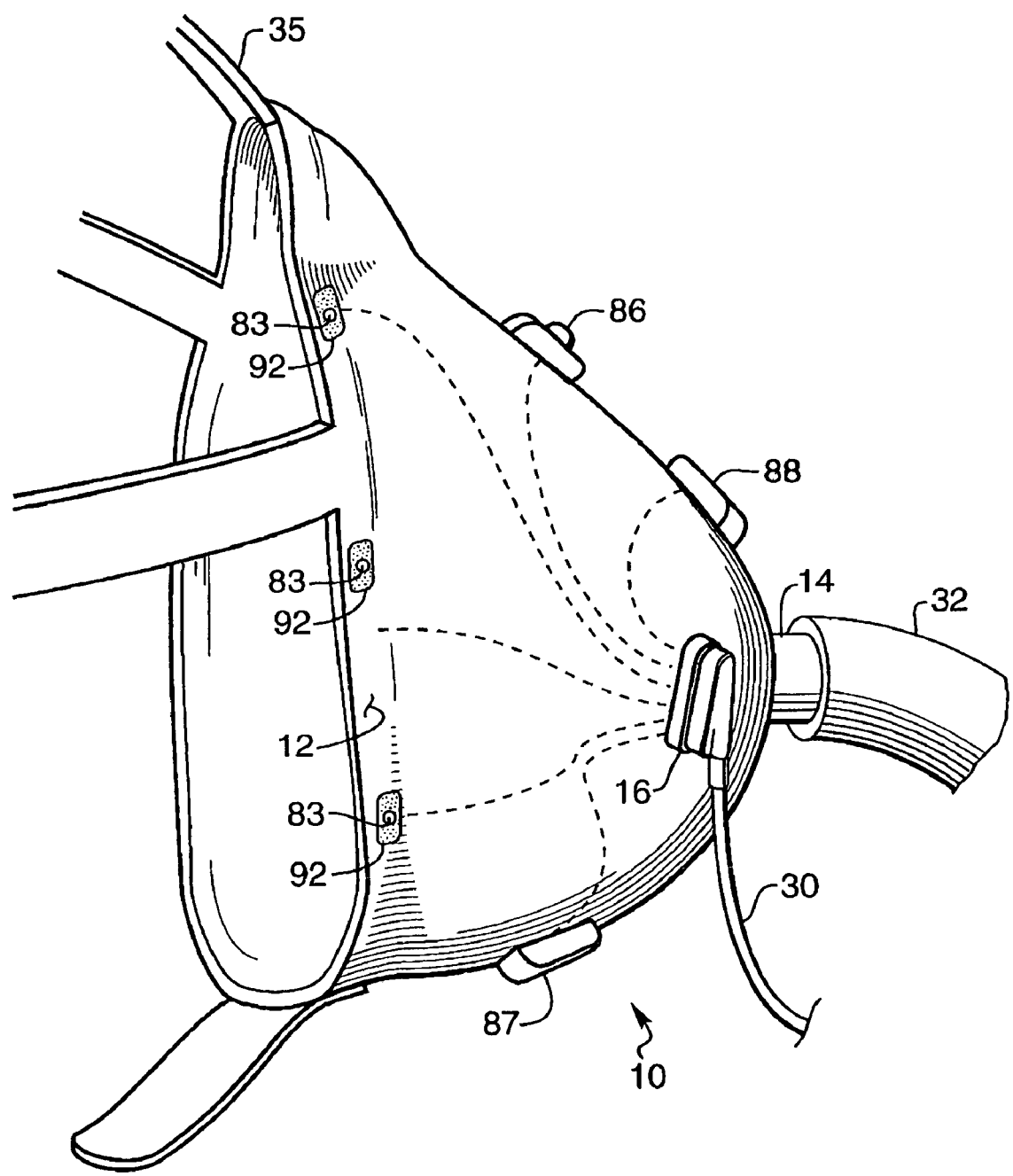
FIG. 7 shows a side schematic view of the mask with sensors on the surface of the mask.

FIG. 7 shows thermal sensors 83 such as thermistors or thermocouples on the inside or outside of the mask adjacent the perimeter 12. These sensors can be attached to a thermally conductive material 92 around the perimeter of the mask 10. Alternatively the thermally conductive material may be on portions of the perimeter. This thermally sensitive material can be on the inside surface of mask 10, the outside surface of mask 10 or embedded within the mask material. Detection of a temperature change by thermal sensors 83 or thermal sensors 83 on thermally conductive material 92 correlates with mask leakage around the perimeter. The thermally sensitive material may be a thermally sensitive material in the mask on the inside of the mask, on the outside of the mask or on the perimeter of the mask. The thermally sensitive material may be a thermistor, a thermocouple, or any other thermally sensitive material.

Gases leaking from the mask 10 will cause a temperature change associated with the thermally conductive material 92 and sensors 83 and allow a healthcare specialist real-time monitoring of leak status or post monitoring status of mask leakage. In some instances this can be life saving where a patient's gas delivery is critical and in other cases the leakage incidence can assist in the diagnosis of a patient. This assistance may be in the form of alerting a health care specialist that the gas delivery was subject to leakage and this may affect patient treatment and patient diagnostic conditions. In other instances the gas leakage detection can allow the gas delivery system to automatically compensate for the gas leakage.

A light sensitive resistor 86 on the outside surface of the mask 10 indicates the ambient lighting conditions of the patient.

Position sensors 87 indicate position or activity of the patient. For example these sensors show if the patient is lying down and is motionless. Such a sensor may be a moving ball across switch contacts, or mercury sensor switches.

Body movement sensor 88 can be a PVD or piezo material or micro mechanical to detect the patients body movements extent and rate to determine a wake versus rest state.

All of the above sensors may send data by telemetry rather than by cable 30.

All of the above collected data may be used to monitor a patient for a variety of uses including sleep studies, anesthesia and sleep apnea.

The data collected can be converted to a serial data stream to allow a single wire to interface all the sensors. The sensors may provide data to adjust gas delivery to the patient.

Gain and filtering adjustments to the signals may be used to condition the signals close to source for optimal noise and signal performance.

An electrical bias to sensors such as a patient position sensors, thermal conductive zones, microphones, or light dependent resistor may be applied.

A computer may process the data or simply store the data to from the monitoring sensors in the mask or straps attached thereto. The monitoring data may be used to diagnose a patient, provide feedback to machines attached to the patient, increase or decrease air supplies to a patient or perform other functions.

An example of EEG data controlling in a bio-feedback application the delivery of gas to a patient may be when a patient has a nasal ventilation device such as a ventilator Continuous Positive Air Pressure (CPAP), Bi-Positive Air Pressure (BIPAP), Variable Positive Air Pressure (VPAP), Sleep Linked Positive Air Pressure (SPAP) and the EEG electrodes provide one of the vital signs of if the patient is asleep. Gas is only applied to the mask when the patient is deemed to be asleep. This function is more sophisticated, sensitive to patient comfort and commercially viable than delay ramp systems used on some ventilation systems.

In ventilation devices that use delay ramps the user sets a time of the system allocates a time and ramps up the gas pressure delivery to the patient so that the application of gas does not have as much disturbing affect on the user and adversely effect his ability to sleep.

The sensors in the mask 10 are better able to determine when the patient is actually asleep before applying assisted nasal ventilation. Premature application of pressure can prevent the patient from sleeping due to the added discomfort of positive pressure.

The mask 10 may be made such that it is a sterile disposable unit for medical use thus lowering costs of treatment by not needing to sterilize masks for new patients and providing a more sterile treatment than reusable masks.

Obviously, many modifications and variations of the present invention are possible in light of the above teachings. It is therefore to be understood that, within the scope of the appended claims, the invention may be practiced otherwise than as specifically described.

What is claimed is:

1. A system for monitoring a patient during gas delivery comprising:
   a breathing mask including a body having an internal surface, an external surface, and a perimeter surface shaped to form a seal around the patient's nose; and a headgear adapted to retain the body on the patient's head, the headgear having at least one EEG sensor positioned thereon to detect brain activity;

a processor adapted to receive a signal from said at least one EEG sensor, said processor determining said patient's sleep stage based at least in part on said signal; and a gas delivery device in communication with said breathing mask, said gas delivery device delivering gas to the patient based on a processor determination of said patient's breathing and sleep stage.

2. The system of claim 1, wherein the headgear is a cap.

3. The system of claim 1, wherein the perimeter surface is adapted to detect ECG.

4. The system of claim 1, and further comprising a flow sensor connected to the internal surface.

5. The system of claim 1, and further comprising an oxygen saturation sensor extended from the mask.

6. The system of claim 1, wherein the perimeter surface is adapted to detect muscle movements.

7. A nasal ventilation system comprising:

a mask including a body having an internal surface, an external surface, and a perimeter surface adapted to form seal around a patient's nose, an airhose extending from the body;

a headgear adapted to retain the body on the patient's head, the headgear having at least one EEG sensor positioned thereon to detect brain activity;

at least one EMG sensor connected to the body and positioned to detect muscle activity relating to a sleep stage;

a processor in communication with said at least one EEG sensor and said at least one EMG sensor, said processor determining said patient's sleep stage based at least in part on a signal received from said at least one EEG sensor; and a gas delivery device in communication with said mask, said gas delivery device changing a delivered air pressure to said patient based on a sleep stage determination by said processor.

8. The system of claim 7, and further comprising a first sensor positioned on the internal surface for detecting nasal breathing and a second sensor positioned on the external surface for detecting oral breathing.

9. The system of claim 8, wherein the first and second sensors are thermal sensors.

10. The system of claim 7, and further comprising at least one EEG sensor positioned on the perimeter surface.

11. The system of claim 7, and further comprising at least one EOG sensor positioned on the perimeter surface.

12. The system of claim 7, wherein a portion of the perimeter surface is comprised of a conductive carbonized rubber material.

13. The system of claim 7, and further comprising a plurality of straps coupled to the body, the straps having at least one sensor positioned thereon.

14. The system of claim 7, and further comprising a position sensor coupled to the body.

15. The system of claim 7, and further comprising a microphone coupled to the body.

16. The system of claim 7, wherein the perimeter surface is provided with a thermally sensitive material, and wherein said system adjusts a gas pressure based on a processor determination of an air leak as indicated by a change in said thermally sensitive material.

17. The system of claim 7, and further comprising a patient recycled air detection system positioned on the internal surface.

18. A nasal ventilation mask assembly comprising:

a nasal mask adapted to form a seal around a patient's nose;

a headgear adapted to retain the body on the patient's head, the headgear having an EEG sensor positioned thereon to contact a patient's forehead upon application of the nasal mask;

a processor adapted to receive signals from said EEG sensor and to determine said patient's sleep stage;

a gas delivery device in communication with said nasal mask, said gas delivery device changing a delivered gas pressure to said patient based on said processor determination of said patient's sleep stage.

19. The mask assembly of claim 18 and further comprising a computer in communication with the sensor, the computer adapted to determine arousal.

20. The mask assembly of claim 18 and further comprising an EMG sensor coupled to the nasal mask.

21. A breathing mask assembly for monitoring a patient during gas delivery comprising:

a body having an internal surface, an external surface, and a perimeter surface shaped to form a seal around the patient's nose and mouth;

a headgear adapted to retain the body on the patient's head, the headgear having at least one EEG sensor positioned thereon so as to be positioned on a top portion of a patient's head;

a processor adapted to receive a signal from said at least one EEG sensor, said processor determining said patient's sleep stage based at least in part on said signal;

and a gas delivery device controlled by said processor to adjust gas pressure delivered to said patient based at least in part on a determination of said patient's sleep stage.

22. A nasal ventilation system comprising:

a nasal mask adapted to form a seal around a patient's nose, the nasal mask having a body, an internal surface, an external surface, and a perimeter surface;

a headgear adapted to retain the body on a patient's head, the headgear having at least one EEG sensor positioned thereon so as to be positioned on a top portion of a patient's head;

an EMG sensor located on the perimeter surface;

a computer in communication with the EEG and EMG sensor, the computer adapted to determine sleep state based on an EEG signal and EMG signal of said patient; and a gas delivery device in communication with said nasal mask and said computer, said gas delivery device adjusting a flow of air to the patient based on determined sleep stages of said patient.

23. The system of claim 22, and further comprising a sensor located on the external surface for determining if a patient is breathing through his mouth.

24. The system of claim 22, and further comprising a flow sensor located on the internal surface.

* * * * *